United States Patent [19]

Hashiguchi et al.

[11] Patent Number: 4,850,342
[45] Date of Patent: Jul. 25, 1989

[54] HARD ENDOSCOPE OF OBLIQUE VIEW TYPE

[75] Inventors: Toshihiko Hashiguchi, Sagamihara; Yoshie Ikegami; Kesao Isono, both of Ina, all of Japan

[73] Assignee: Olympus Optical Co., Ltd., Tokyo, Japan

[21] Appl. No.: 722,425

[22] Filed: Apr. 12, 1985

Related U.S. Application Data

[63] Continuation of Ser. No. 490,420, May 2, 1983, abandoned.

[30] Foreign Application Priority Data

May 1, 1982 [JP] Japan .................................. 57-74239

[51] Int. Cl.$^4$ .............................................. A61B 1/06
[52] U.S. Cl. ......................................................... 128/6
[58] Field of Search .......................................... 128/4–8

[56] References Cited

U.S. PATENT DOCUMENTS

| | | | |
|---|---|---|---|
| 2,932,294 | 4/1960 | Fourester et al. | 128/6 |
| 3,297,022 | 1/1967 | Wallace | 128/6 |
| 3,556,085 | 1/1971 | Takahashi | 128/6 |
| 4,176,661 | 12/1979 | Schubert et al. | 128/6 |

FOREIGN PATENT DOCUMENTS

| | | | |
|---|---|---|---|
| 2249641 | 5/1975 | France | 128/7 |
| 58-12642 | 1/1983 | Japan . | |

Primary Examiner—Max Hindenburg
Attorney, Agent, or Firm—Armstrong, Nikaido, Marmelstein, Kubovcik & Murray

[57] ABSTRACT

A hard endoscope of oblique view type which provides equal illumination of the range of visibility of the objective optical system. The endoscope has an exterior tubular member with an interior housing member disposed eccentrically within the tubular member and carrying an inspection optical system, with the distal end of the endoscope terminating in an oblique planar surface. Illuminating means are carried between the housing member and the exterior tubular member. In the region of the oblique planar surface, the interior of the tubular member and the exterior of the housing member define a passage for the illuminating means having a generally crescent-shap, or, preferably, two cylindrical surfaces in which the illuminating means are carried to transmit light from the oblique planar surface that will transmit light to produce the image of the illumated object, so that it may be clearly seen by the inspection optical system.

11 Claims, 5 Drawing Sheets

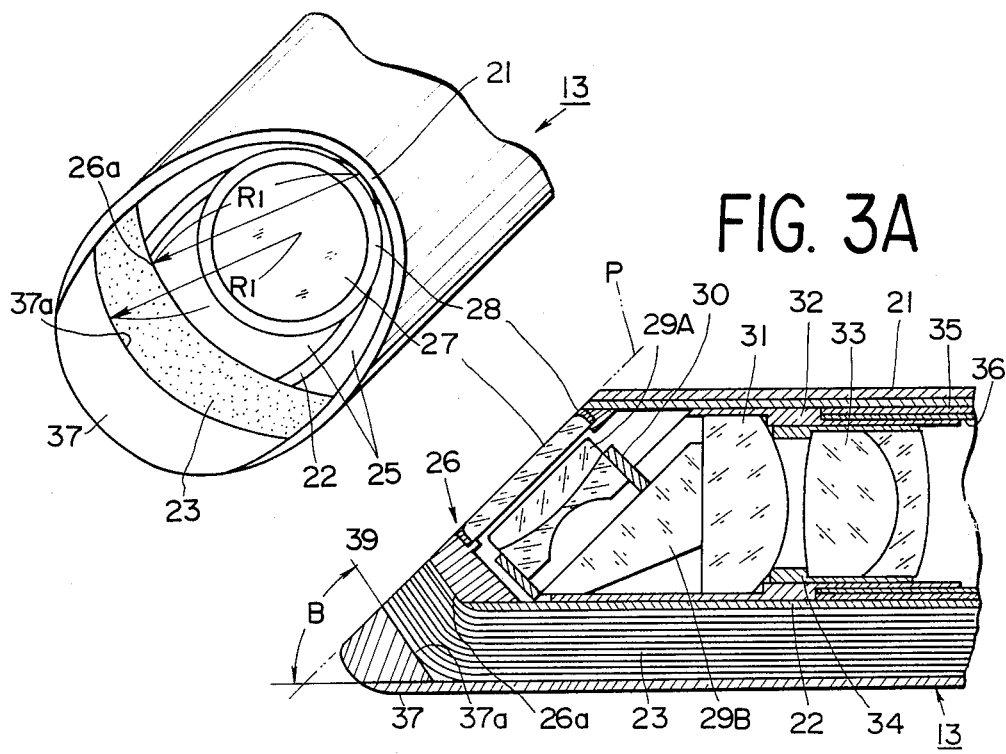
FIG. 3B
FIG. 3A
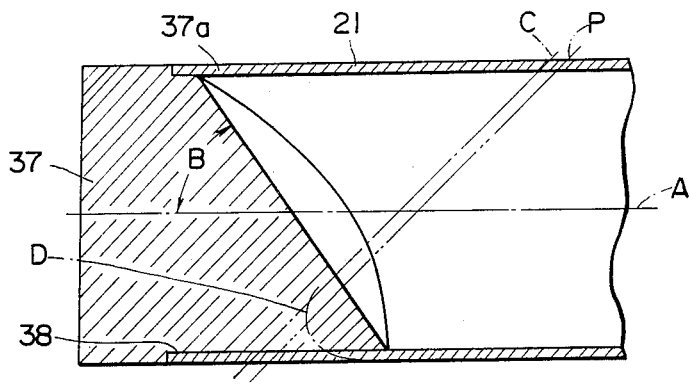
FIG. 4

HARD ENDOSCOPE OF OBLIQUE VIEW TYPE

This application is a continuation of application Ser. No. 490,420 filed May 2, 1983 now abandoned.

BACKGROUND OF THE INVENTION

The present invention relates to a hard endoscope oblique view type which permits the illumination to lighten equally the visible range.

In recent years, endoscopes are widely employed for inspecting and diagnosing the intracavitary organs, intraorganic wallsurface or other objectives by introducing a tubular insert into the corporal cavity. Also in industrial field, endoscopes are employed to inspect inside of the tubes of boiler, machines, chemical plants etc.

These endoscopes include structurally the illuminating optical system for ejecting the illuminating light from the objective side of the top end of housing after transmitting the illuminating light supplied to the observer's side when having inserted the tubular housing, and the inspecting optical system for inspecting from the rear of the eye-piece on the observer's side through the image-transmitting means after having focussed the image of objective illuminated by said illuminating optical system.

In order to inspect appropriately according to the object in a desired region through the openings at respective top ends of said illuminating optical system and the inspecting optical system; the endoscopes for inspecting axial direction in front of the tubular housing through the inspection opening with the illuminating light are classified into the direct view type formed opposite to the object, the lateral view type formed along the lateral of the tubular housing and the oblique view type inclined with a predetermined angle to the axial direction of the tubular housing.

The tubular housing of the endoscope formed with an opening for inspecting each direction of view field, when inserted by the guides of soft endoscope with a flexible tubular housing and of trachea etc., is sometimes formed rigid in a substantially linear shape to facilitate its introduction into the cavity.

In the hard endoscope of oblique view type, in view of conventional techniques, the inner tube is passed through with the outer tube having the inspecting optical system inside, while the illumination-transmitting means is passed through the cavity of substantially crescent cross section between the circumference of the outer tube and the outer circumference of said inner tube. The present endoscope is so composed that the object illuminated with the light ejected from the top end surface of said transmission means may be inspected with said inspecting optical system. However, in the endoscope of oblique view type as disclosed in said conventional techniques or in Japanese Pat. Application Disclosure No. 12,642/58, the illuminating light ejected from the top end of the illumination-guiding fiber as the transmission means for inspection-range directed to the front of oblique direction is diffused too much in the direction curved obliquely and cannot illuminate equally the inspection range. Accordingly even if the image of the object is caught in the field of view, it is often difficult to inspect sufficiently clearly and so a diagnose is a little difficult. In this way, the function of the inspecting optical system is insufficiently performed, but a highly complete endoscope of oblique view type is required. Furthermore it is difficult to maintain the axial direction of illumination with high accuracy from view-point of the production of endoscope.

BRIEF SUMMARY OF THE INVENTION

An object of the present invention is to propose a hard endoscope of oblique type which can illuminate equally the inspection range.

Another object of the present invention is to propose an endoscope of oblique view type which lessens the dispersion of ray in the illumination direction.

A further object of the present invention is to propose an endoscope of oblique view type which lessens the dispersion of the number of illumination fibers arranged in the light-transmission distance when compared between different products.

BRIEF DESCRIPTION OF THE DRAWINGS

FIGS. 2-5 relate to Example 1 of the present invention.

FIG. 2 is a diagrammatic sketches showing the hard endoscope of oblique view type in Example 1.

FIG. 3 is a magnified diagram for the front end of the tubular housing.

FIG. 3(a) shows an elevational cross section.

FIG. 3(b) is oblique view aspect from oblique view direction in FIG. 3(a).

FIG. 4 is an elevational cross section showing a machined work material for forming the outer tube in Example 1, FIG. 5 is a diagram for explaining the working process to form the housing member in Example 1, FIG. 5(a) showing the lateral elevational view of the housing member, FIG. 5(b) showing the front view of the housing member.

DETAILED DESCRIPTION OF THE INVENTION

Figure 1:
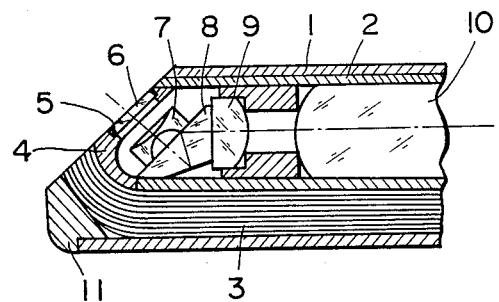
FIG. 1 is a cross section view showing the front end of the hard endoscope of oblique view type in the conventional technical examples.

Before each Example of the present invention will be described, an Example of conventional technique for the hard endoscope of oblique view type is described in reference to FIG. 1.

Inner tube 2 including the inspecting optical system is arranged eccentrically inside outer tube 1 of the prolonged tubular housing, furthermore an illumination-guiding fiber 3 for transmitting the illuminating light supplied to one end surface (not presented in the drawings) and for ejecting from the top end is passed through the substantially crescent-cross sectioned cavity and outer periphery of the inner tube 2.

An opening obliquely notched rectangularly to the inspecting view direction is formed in the top end of said outer tube 1. Support member 4 with an inspection opening and forming a notched hemispheric member is mounted to the top end of inner tube 2 arranged inside said opening.

Said opening bored in the support member 4 is fixingly fitted with a cover glass 6 by intermediate of a fixed frame 5. In the space which is sealed with said cover glass 6, the optical image of the object positioned ahead of view field inclined to the axial direction of the tubular housing is focussed in rear of axial direction of the tubular housing through the objective optical system formed of the objective front-lens 7, objective prism 8 and objective rear-lens 9, and then is transmitted to the eyepiece system through relay-lens system 10 as an image-transmitting lens.

The top end of illumination-guiding fiber 3 arranged about the periphery of said inner tube 2 is guided and curved along the inner periphery of chip member 11 mounted to both outer periphery of support member 4 and the top end of outer tube 1 so as to illuminate from the outer periphery of cover glass 6 to front of oblique direction.

In respect to thus composed conventional hard endoscope of oblique type, since the curvature of the outer peripheral surface of support member 4 is different from the curvature of the inner peripheral surface of the chip member 11, the illumination-guiding fibers 3 about the top end are not arranged in parallel. Therefore the illumination light ejected from the top end surface of the illumination-guiding fiber 3 is dispersed out of the focussing range of the objective optical system and objects cannot be seen and cannot illuminate evenly the visible range. Accordingly the object region to be inspected is difficult to be observed clearly. Also it is difficult to assure high accuracy in the direction of illuminating center line when producing endoscopes. The present invention is designed to solve the difficulties found in the conventional technique.

Figure 2:
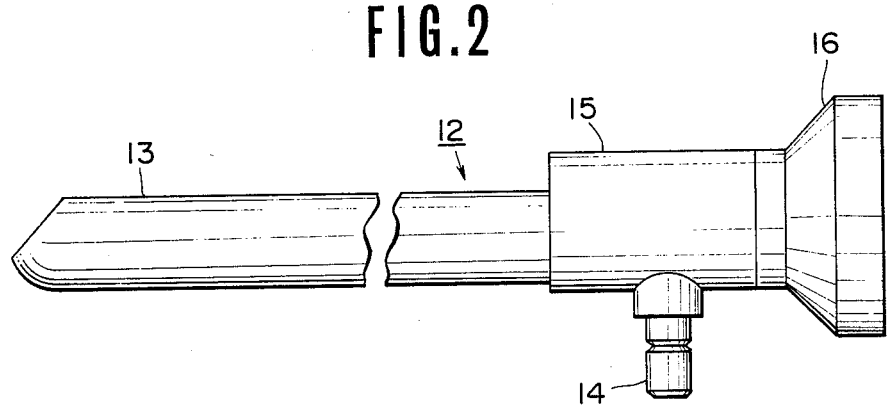

Each Example of the present invention will hereafter be described in reference to the drawing of FIG. 2 and further drawings.

In FIG. 2, the hard endoscope of oblique view type in Example 1 is composed of a prolonged tubular housing 13, an operation section 15 with a illumination-guiding mouth piece 14 projected from the lateral side of the rear end of said housing 13, and an eyepiece section 16 containing the eyepiece optical system (not presented in the drawing) at the rear end of said operation section 15.

In FIG. 3, said tubular housing 13 is covered with a hard outer tube 21, in which the inner tube 22 containing the inspecting optical system is arranged eccentrically in contact with the upper inner peripheral surface of outer tube 21. In the outer tube 21 about the outer periphery of inner tube 22, an illumination-guiding fiber 23 for transmitting the illumination supplied to said illumination-guiding mouth piece 14 through the illumination-guiding cable (not presented in the drawing) extends along an axially extending passage defined by the exterior of the interior housing member 22 and the interior of the exterior tubular member 23 to a terminal portion of said passage in the proximity of the oblique planar surface at the distal extremity of the endoscope where the passage is curved to intersect the oblique planar surface.

The top end of said outer tube 21 is notched with a cross section rectangular to the inspecting view direction and is opened and forms an oblique view surface inclined with a predetermined angle to the axial direction of tubular housing 12. The top end of the inner tube 22 arranged eccentrically inside the obtained opening is bored with an inspection opening. A top end member 25 for the inner tube with its flange attached to the inner periphery of said opening is incorporated to form a housing member 26 substantially tubular containing an inspection optical system. A cover glass 27 with its partial outer periphery cut open in taper is mounted to the opening in the top end member 25 of said inner tube by pushing a fastening ring 28 into said opening to press the tapered peripheral edge of said cover glass 27 to make the peripheral edge of the other surface butt onto said tapered peripheral edge.

An objective optical system as will be described below is contained inside the opening sealed with said cover glass 27. An objective front lens 29A arranged in parallel with the plane of cover glass 27 at a slight gap is fixed to the objective prism 29B with a frame 30.

An objective lens 31 s butted on the back plane of objective prism 29B arranged rectangular to the housing 13. The periphery of said objective lens 31 is fixed to the objective external frame 32. An objective rear-lens 33 separated from said objective lens 31 at a predetermined distance is fixed to said objective external frame 32 by intermediate of the objective middle frame 34.

Said objective external frame 32 is fitted to the inner tube 22. The rear end of said objective external frame 32 is diametrically reduced stepwise and fitted and connected backwards to the inner peripheral surface of tubular container 35 containing relay optical system (not presented in the drawing) by intermediate of ring spacer 36.

The tubular member of the present invention is composed in the manner that the top end member 37 of the external tube is attached to be top end of external tube 21 about the outer periphery near the lower section or bottom plane separated from the containing member 26 incorporated with the top end member 25 of the inner tube 22 to form the container member 26 for the optical system.

The top end of said outer tube 21 and the top end member 37 of the outer tube are, for example, formed as shown in FIG. 4. A cylindrical top end member 37 of the outer tube formed as the fitting section 38 having an outer diameter substantially fittable to the inner diameter of said outer tube 21 is connected to the top end of the outer tube 21 with such plumb joint or solder as silver solder at said fitting section 38.

The end plane of the top end member 37 of the outer tube to be connected with the fitting section 38 to the outer tube 21 is formed with the cylindrical surface 37a of a radius $R_1$ inclined by an angle B (as shown in FIG. 3) relative to the center axis A of the outer tube 21. The tubular housing is notched at an angle substantially rectangular to said cylindrical surface 37a to form the end surface C for inspection before polishing and for illumination. Said top end member 37 of the outer tube is exposed only in the lateral lower part near bottom plane projected forwards from the end plane C. This part projected with a sharp angle of the top end member 37 has its edge rounded, as shown with chain line D, lest human organs should be injured at the time of introducing into cavities.

The end plane C notched as above mentioned, after arranged with the illumination-guiding fiber 23, is polished till the part as shown with double-dotted chain line P to form the end plane 39 for illumination and inspection or oblique view as shown in FIG. 3. In this way, the outer tube 21 is incorporated with the top end member 37 of the outer tube of a predetermined shape, and the tubular member is so formed as to pass through with both containing member 26 and the illumination-guiding fiber 23. In this case, the inner periphery of the end surface of said top end member 37 for said outer tube becomes a cylindrical surface 37a of a radius of curvature $R_1$ as shown FIG. 3.

On the other hand, the top end member 25 is incorporated with the inner tube 22 to form a containing member 26 of substantially tubular shape as shown in FIG. 5.

Figure 5A:
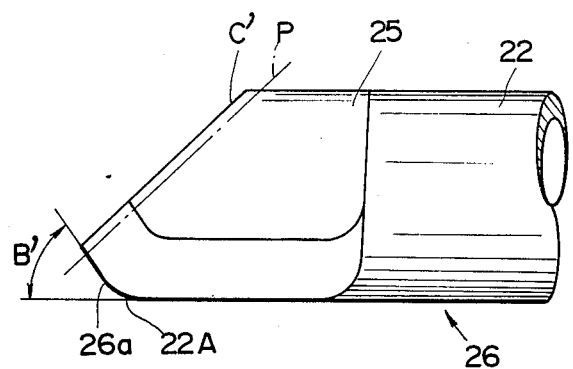
Figure 5B:
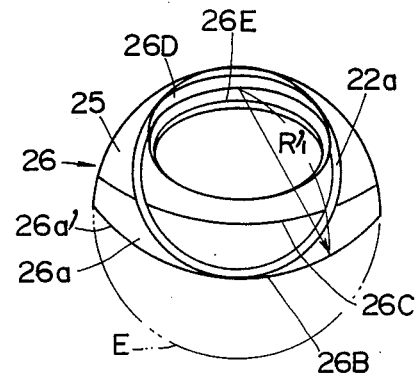

As shown in FIG. 5, the top end of the inner tube 22 is fixed to the rear end of the part of an outer diameter equal to the inner diameter of the outer tube 21 in the direction rectangular to the plane of diagram as shown with the double-dotted chain line E in FIG. 5(b), and the front side of said cylindrical member is shorn along an inclined plane C' (see FIG. 5(a)) while leaving a margin for polishing abrasion (thicker portion), and moreover said cylindrical member is cut with a radius of curvature $R_1$ about the substantial center axis of cylindrical surface or about the direction of inspecting field of view to form a cylindrical surface 26a on the lower side (or near bottom plane) with an angle B' (equal to angle B) to the axial direction of the inner tube 22. Furthermore a cylindrical surface 26a' of a radius of curvature R' with the center axis parallel with the center axis of the inner tube 22 is formed in contact with the lower part of the inner tube 22 by machining. In this case, reference numbers 26B, 26C in FIG. 5(b) indicate respective boundaries of said cylindrical surfaces 26a' and 26a'. A cylindrical opening section for inspection is formed on substantial central upper side of said inclined plane C'. When said inclined plane C' is ground to reduce only the predetermined thickness for polishing work, after the housing member 26 has been eccentrically passed through the outer tube 21, the product of Example 1 is obtained with the structure as shown FIG. 3.

On the other hand in FIG. 5(b), a concave facing 26D to be pushed in with a ring fastener 28 for the cover glass 27 and a flange 26E projected inwards from said concave facing 26D are shown on the inner peripheral surface in the inspection opening. Furthermore the end plane 22a of the inner tube 22 is exposed as a ring in the inclined plane C' and in the cylindrical plane 26a. The common boundary of cylindrical surface 26a of the top end member 25 for the inner tube incorporated with the top end of the inner tube 22 and of the outer periphery of the inner tube 22 exposed on the outer periphery of said cylindrical surface 26a is rounded as shown with reference No. 22A in FIG. 5(a).

In respect to the top end member 25 projected on the outer periphery of said inner tube 22, the outer peripheral part on upper side of the inner tube 22 has smaller wall thickness, while both sides of the outer peripheral parts has larger wall thickness. The gap of substantial crescent profile in cross section between the inner peripheral surface of the outer tube 21 and the outer peripheral surface of the inner tube 22 is blocked from outer peripheries on both sides of the inner tube to the outer periphery on the upper side near the top end, but the lower side of the top end member 25 of the inner tube is rounded on the rear end side. The illumination-guiding fibers 23 passing through along the substantial crescent gap in the outer periphery of said inner tube 22 from the observer's side are collected together through the lower side of the inner tube 22 by the top end member 25 blocking both sides of the inner tube 22 and the outer periphery on the upper side near the top end. To speak in short, the illumination-guiding fibers 23, near their ejection end surface, pass through the gap in the manner that the cross section area formed between said cylindrical surface 26a or the outer peripheral surface on the lower side of the top end member 25 of the inner tube and the cylindrical surface 37a or the inner peripheral surface of the top end member 37 of the outer tube may be constant.

In this way, according to Example 1 the top end member 25 mounted to the top end of the housing member 26 containing the inspecting optical system is so adapted that its peripheral surface along the inspection field of view may be a cylindrical surface 26a. Also the top end member 37 mounted to the top end of the outer tube 21 has the cylindrical surface 37a substantially equally distanced as said cylindrical surface 26a. Therefore the ejection end of the illumination-guiding fibers 23 arranged filling between both cylindrical surfaces 26a, 37a are so adapted that the fibers may be parallel together along the direction of inspection field of view. That is why the illumination light ejected from the end surface of the fibers 23 is directed along the inspection field of view and does not disperse too much and therefore it is focussed by the objective optical system so that it may illuminate effectively and equally the visible field of view.

According to Example 1, the air gap in which the ejection end is formed by the arrangement of the illumination-guiding fibers 23 is limited by both cylindrical surfaces 26a and 37a, and the area of its cross section is constant in spite of the processing dispersion of the fibers so that the number of the illumination-guiding fibers 23 to fill the gap may be constant. It is advantageous, therefore, that the deficient illumination or dispersed illumination never occurs. Also the center of illuminating direction is much stable.

Angles B and B' between each cylindrical surface 26a or 37a and the central axis of the outer tube 21 are equal to or larger than the angle between the direction of the inspection field of view and the central axis of said outer tube 21. Accordingly in the case of these angles B, B' being equal to the angle of inspection field of view, the center of inspection field of view hardly deflects from the center of illumination range for the object far-distanced from the top end of the tubular housing. However in the case of angles B, B' being larger than the angle of inspection field of view, the direction of inspection field of view intersects with the illumination direction at the position near to the top end of the tubular housing, and an excellent quality of illumination is obtained without difference of the center of inspection field of view with the center of illumination range at the position of intersection. Therefore an excellent illumination is obtained in different cases when angles B, B' are selected appropriately depending on whether the object to be inspected is distant or near.

Figure 6:
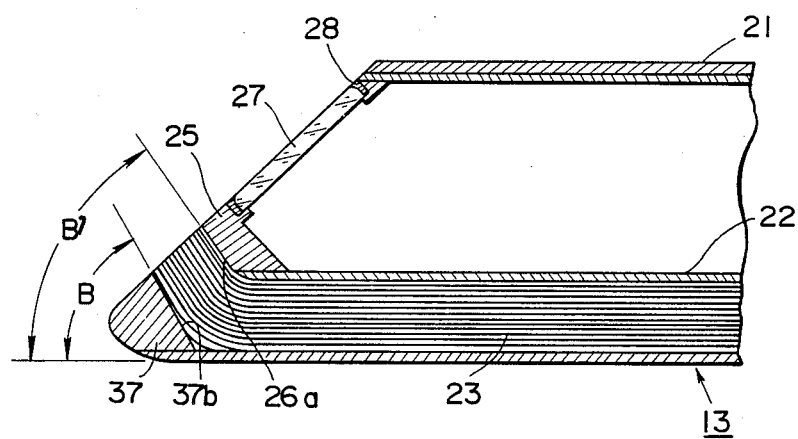
FIG. 6 is elevational cross section view showing the top end of the tubular housing in Example 2 of the present invention.

In Example 2 as shown in FIG. 6, the inclination angle B of the top end member 37 of the outer tube to the axial direction of tubular housing 13 of cylindrical surface 37b is slightly larger than the inclination angle B' of the cylindrical surface 26a of the top end member 25 of the inner tube composing the housing member 26. Otherwise the inclination angle B' on the side of cylindrical surface 26a may be smaller than the inclination angle B.

According to this Example, the cross section area of the housing section of illumination-guiding fibers 23 is smaller as approaching to the end surface of illumination-guiding fibers 23. At the same time the filling percentage of the end surface of illumination-guiding fibers 23 grows higher, and in the case of polishing the end surface for wider gap, it is prevented that filled adhesive agent is abrased too much and the top surface may become rugged.

In this Example, other details are the same with Example 1, and the same elements have the same reference numbers. In FIG. 6, the inspection optical system is not presented.

Figure 7:
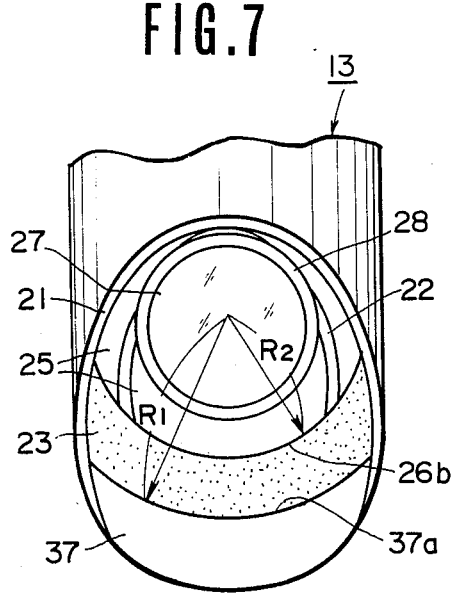
FIG. 7 is oblique view aspect showing the top end of the tubular housing in Example 3 of the present invention.

In Example 3, as shown in FIG. 7 the radius of curvature $R_2$ of cylindrical surface 26b of the top end member 25 of the inner tube is smaller than the radius of curvature $R_1$ of cylindrical surface 37a of the top end member 37 of the inner tube, and the center of both cylindrical surfaces 26b and 37a are identical.

Figure 8:
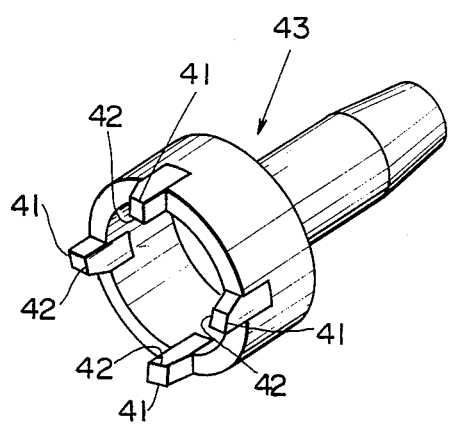
FIG. 8 is oblique view aspect showing the tool for effecting Example 3 in the present invention.

Accordingly in the case of shaping both cylindrical surfaces 26b, 37a, as shown in FIG. 8 for example, plural cutting edges having each cutting element 41 for machining the internal wall of a radius of curvature $R_1$ and each cutting element 42 for machining the outer peripheral surface of a radius of curvature $R_2$ are mounted to the cylindrical end surface. If the cutting tool 43 can cut the material coming in contact with the cutting edge by rotation, both cylindrical surfaces 26b, 37a are machined with a single tool 43 to effect the cost reduction.

Figure 9:
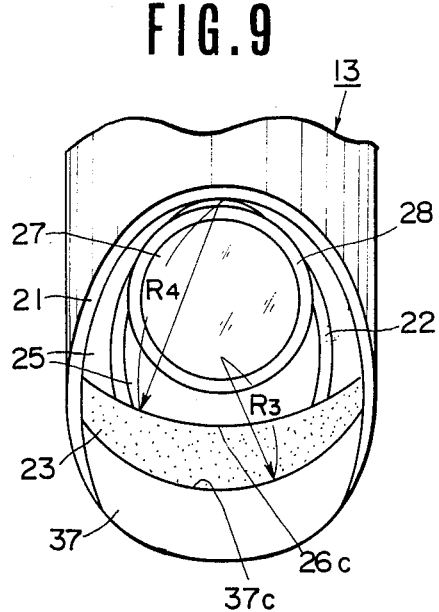
FIG. 9 is oblique view aspect showing the top end of the tubular housing in Example 4 of the present invention.

In Example 4 as shown in FIG. 9, the radius of curvature $R_3$ of cylindrical surface 37c of the top end member 37 of the outer tube is smaller than the radius of curvature $R_4$ of cylindrical surface 26c of the top end member 25 of the inner tube.

In other words, the profile of empty space between both cylindrical surfaces 26c, 37c, wherein the illumination-guiding fibers 23 are passed through the form the ejection end surface, is substantially crescent and it resembles the shape of cross section of illumination-guiding fibers 23 which is passed through from the top end of tubular housing 13 backwards. Therefore when the illumination-guiding fibers 23 are inserted through, the shape of the part to be curved changes slightly and so the assemblage process is advantageously simple.

Figure 10:
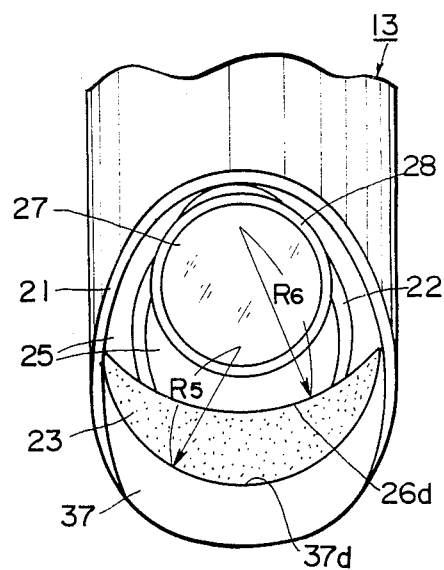
FIG. 10 is oblique view aspect showing the top end of the tubular housing in Example 5 of the present invention.

In Example 5 as shown in FIG. 10, the radius of curvature $R_5$ of cylindrical surface 37d of the top end member 37 of the outer tube is a half of the inner diameter of the outer tube 21, and the radius of curvature $R_6$ of cylindrical surface 26d of the top end member 25 of the inner tube is equal to the radius of curvature $R_1$ of cylindrical surface 26a on the side of top end bottom surface of the top end member 26 of said inner tube as shown FIG. 5.

According to this manner of construction, the cross sectional profile of the curved part around the ejection end of illumination-guiding fibers 23 does not change to facilitate the inspection process of illumination-guiding fibers 23 very much.

Figure 11A:
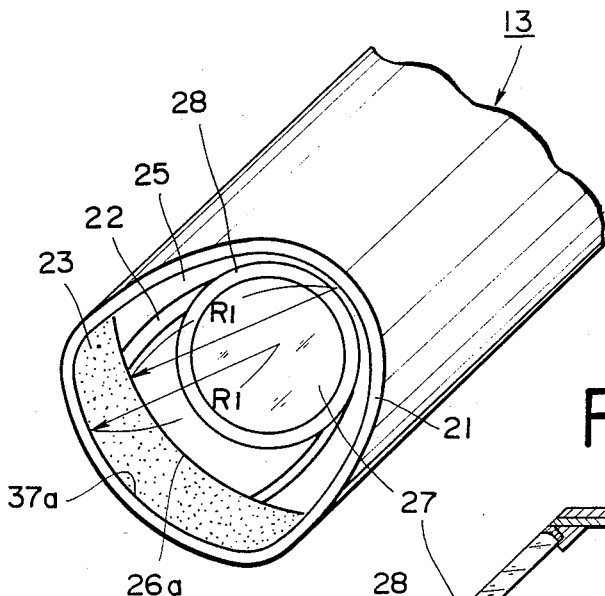
FIG. 11(a) is elevational cross section showing the top end of the tubular housing, FIG. 11(b) being oblique view aspect from oblique view direction of FIG. 11(a).
Figure 11B:
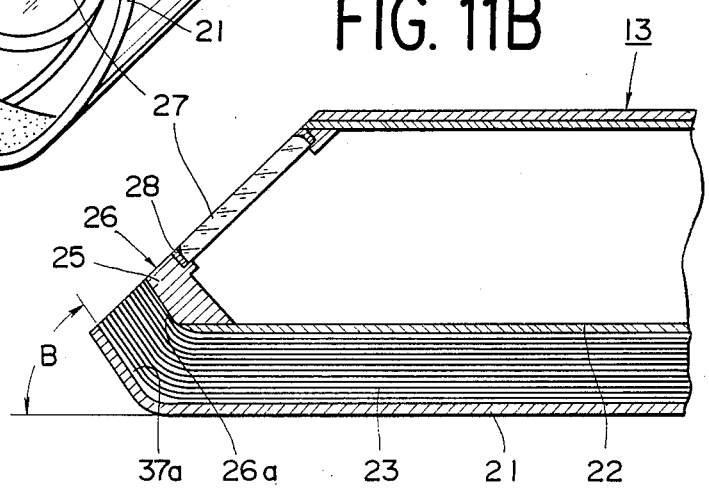
FIG. 11 relates Example 6 of the present invention.

In Example 6 as shown in FIG. 11, the production process comprises inserting the front end of the outer tube 21 into a mold under pressure without employing the top end member 37 for the outer tube and molding curvingly the cylindrical surface 37a.

According to this Example, since a connection part to be prepared by silver soldering or plumb soldering etc. does not exist, it is prevented that the top end member 37, if employed, may be deserted in body cavity, and so that user can easily employ the endoscope without fail. The rest description of Example 6 will be all the same with Example 1 as shown in FIG. 3. The inspection optical system is not presented in FIG. 11.

Said means for molding curvingly the top end of outer tube 21 without employing said top end member 37 of the outer tube is obviously applicable to other Examples.

In the above description, both the outer peripheral surface of the top end of housing member 26 and the top end member 37 of outer tube or the inner peripheral surface of the top end of outer tube 21 are expressed as cylindrical surfaces, but the case of expressing only one of these surfaces as cylindrical surface and the other as substantial cylindrical surface may be included in the scope of the present invention. Also the present invention indicates the relay lens system as the image-transmitting means for the inspection optical system, but the resent invention is not limited within these Examples nor to the constitution of objective optical system.

Furthermore the tubular member described in "What is claimed" may be of course the outer tube 21 covering the tubular housing (Ref. No. 13 in FIGS. 2 and 3) or the outer tube 21 incorporated with the top end member 37 of the outer tube, but also the outer tube 21 inserted through into the tubular housing 13.

As mentioned above, according to the present invention the empty space containing the illumination-guiding fibers with the ejection end is limited by the cylindrical surfaces in parallel or substantially parallel together, and the illumination-light ejected from the end surface of illumination-guiding fibers can advantageously illuminate effectively and equally the visible range. As the cross section area of empty space near the ejection end is maintained substantially constant, the number of illumination-guiding fibers is not so dispersed for different products.

Furthermore the direction of illumination is advantageously invariable for different products.

Examples of realization modifiable in wide range can be constructed without deviating from the spirit and scope of the present invention. Therefore the present invention shall not be limited to particular examples of realization as restricted in the attached claims.

What is claimed is:

1. In an endoscope of the oblique view type having an exterior tubular member, a interior housing member carrying an inspection optical system, the distal end of the endoscope terminating in an oblique planar surface, illuminating means for transmitting light to said oblique surface including a plurality of optical fibers, a passage between said exterior tubular member and said interior housing member for carrying said optical fibers, and a curved terminal portion of said passage with said plurality of optical fibers therein in the proximity of said oblique planar surface to intersect with said oblique planar surface and project light in the direction of the inspection field of view, characterized in that said terminal portion of said passage has a shape defined primarily by the cylindrical surface of the exterior of said interior housing member and by the spaced cylindrical surface formed by the interior surface of said exterior tubular member whereby said optical fibers are maintained in substantially parallel relationship throughout said passage and said curved terminal portion to provide effective and equal light throughout the field of view.

2. An endoscope as claimed in claim 1, wherein the axial direction of the terminal portion of said passage is parallel to the direction of the field of view of said inspection optical system.

3. An endoscope as claimed in claim 1, wherein the terminal portion of said passage comprises two cylindrical surface of equal radius.

4. An endoscope as claimed in claim 1, wherein the terminal portion of said passage comprises two cylindrical surfaces with the centers of the radii of curvature at the same point.

5. An endoscope as claimed in claim 1, wherein the terminal portion of said passage comprises two cylindrical surfaces, the cylindrical surface of the interior of the tubular member having a smaller radius than the radius of the cylindrical surface of the exterior of the housing member.

6. An endoscope as claimed in claim 1, wherein the terminal portion of said passage comprises two cylindrical surfaces having the same size and shape as the passage between the interior surface of the tubular member and the exterior surface of the housing member as it exists along most of the axis of the endoscope.

7. An endoscope as claimed in claim 1, wherein the terminal portion of said passage comprises two cylindrical surfaces, and wherein the angle of inclination of the cylindrical surfaces with respect to the axis of the tubular housing are equal.

8. An endoscope as claimed in claim 1, wherein the terminal portion of said passage comprises two cylindrical surfaces and wherein the angle of inclination of the interior cylindrical surface of the exterior tubular member is larger than the angle of inclination of the exterior cylindrical surface of the interior housing member.

9. An endoscope of the oblique view type as claimed in claim 1, wherein the terminal portion of said passage comprises two cylindrical surfaces and wherein the angle of inclination of the exterior cylindrical surface of the exterior tubular member and the axial direction of the interior housing member is equal to the angle of inclination formed between the direction of the inspection field of view and the axial direction of the housing member.

10. An endoscope of the oblique view type as claimed in claim 1, wherein the terminal portion of said passage comprises two cylindrical surfaces, and wherein the angle of inclination formed between the outer cylindrical surface of the exterior tubular member and the axial direction of the interior housing member is larger than the angle of inclination formed between the direction of the inspection field of view and the axial direction of the interior housing member.

11. An endoscope of the oblique view type comprising: an exterior tubular member, an oblique planar surface at the distal end of said exterior tubular member, and interior housing member disposed eccentrically within said exterior tubular member and carrying an inspection signal system with a field of inspection view directed from said oblique surface, illuminating means to provide light to said oblique surface including a plurality of optical fibers, a passage to carry said illuminating means along said endoscope in said exterior tubular member, a terminal portion of said passage curved to intersect said oblique surface and light said field of inspection view, said curved terminal portion of said passage in the proximity of said oblique surface being defined primarily by a cylindrical outer surface of said interior housing member and a spaced cylindrical surface of an inner surface of said exterior tubular member, and said terminal portion of said passage carrying said plurality of optical fibers while maintained in substantially parallel relationship to provide equal illumination throughout said inspection field of view.

* * * * *